United States Patent [19]

Boden et al.

[11] Patent Number: 5,300,489
[45] Date of Patent: Apr. 5, 1994

[54] FRAGRANCE USE OF DIHYDROMETHYL JASMONIC ACID

[75] Inventors: Richard M. Boden, Ocean; Futoshi Fujioka, Oakhurst; Marie R. Hanna, Keyport, all of N.J.

[73] Assignee: International Flavors & Fragrances Inc., New York, N.Y.

[21] Appl. No.: 74,606

[22] Filed: Jun. 11, 1993

[51] Int. Cl.$^5$ .................................. A61K 7/46
[52] U.S. Cl. ........................................ 512/8
[58] Field of Search .............................. 512/8

[56] References Cited

U.S. PATENT DOCUMENTS

| | | | |
|---|---|---|---|
| 3,158,644 | 11/1964 | Demole et al. | 512/8 |
| 3,951,876 | 4/1976 | Celli et al. | 512/8 |
| 3,978,108 | 8/1976 | Teisseire et al. | 512/8 |
| 4,092,362 | 5/1978 | Celli | 512/8 |
| 5,235,110 | 8/1993 | Yamada et al. | 512/8 |

FOREIGN PATENT DOCUMENTS 2824841 2/1978 Fed. Rep. of Germany .......... 512/8

OTHER PUBLICATIONS

Ravid and Ikan "New Syntheses In Dihydrojasmon" series, J. Org. Chem., vol. 39, No. 17, 1974, pp. 2637–2639.

Ikan and Ravid, Chem. Abstracts vol. 84:135148j "Synthesis of Odorous Principles, Dihydrojasmons."

*Primary Examiner*—James H. Reamer
*Attorney, Agent, or Firm*—Arthur L. Liberman

[57] ABSTRACT

Described in the use of dihydromethyl jasmonic acid having the structure:

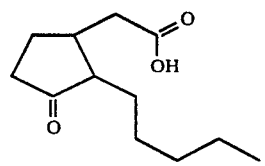

in augmenting, enhancing or imparting fragrances in or to perfume compositions, perfumed articles and colognes.

10 Claims, 6 Drawing Sheets

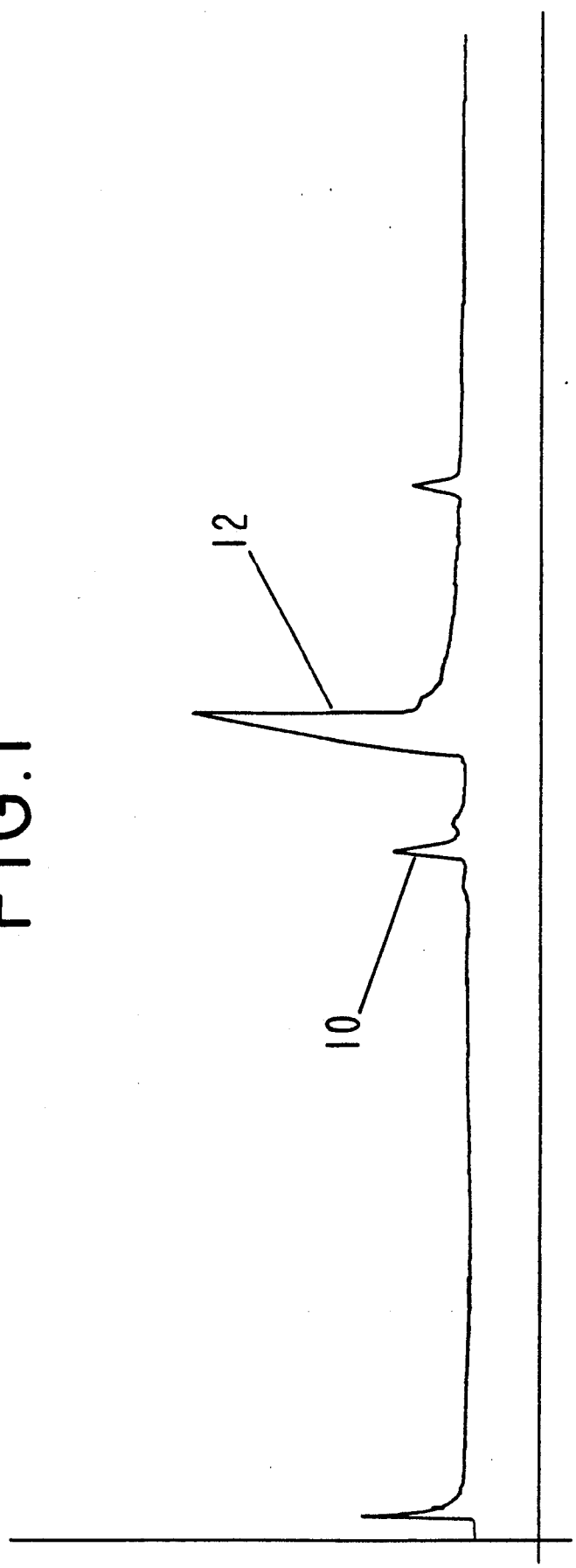

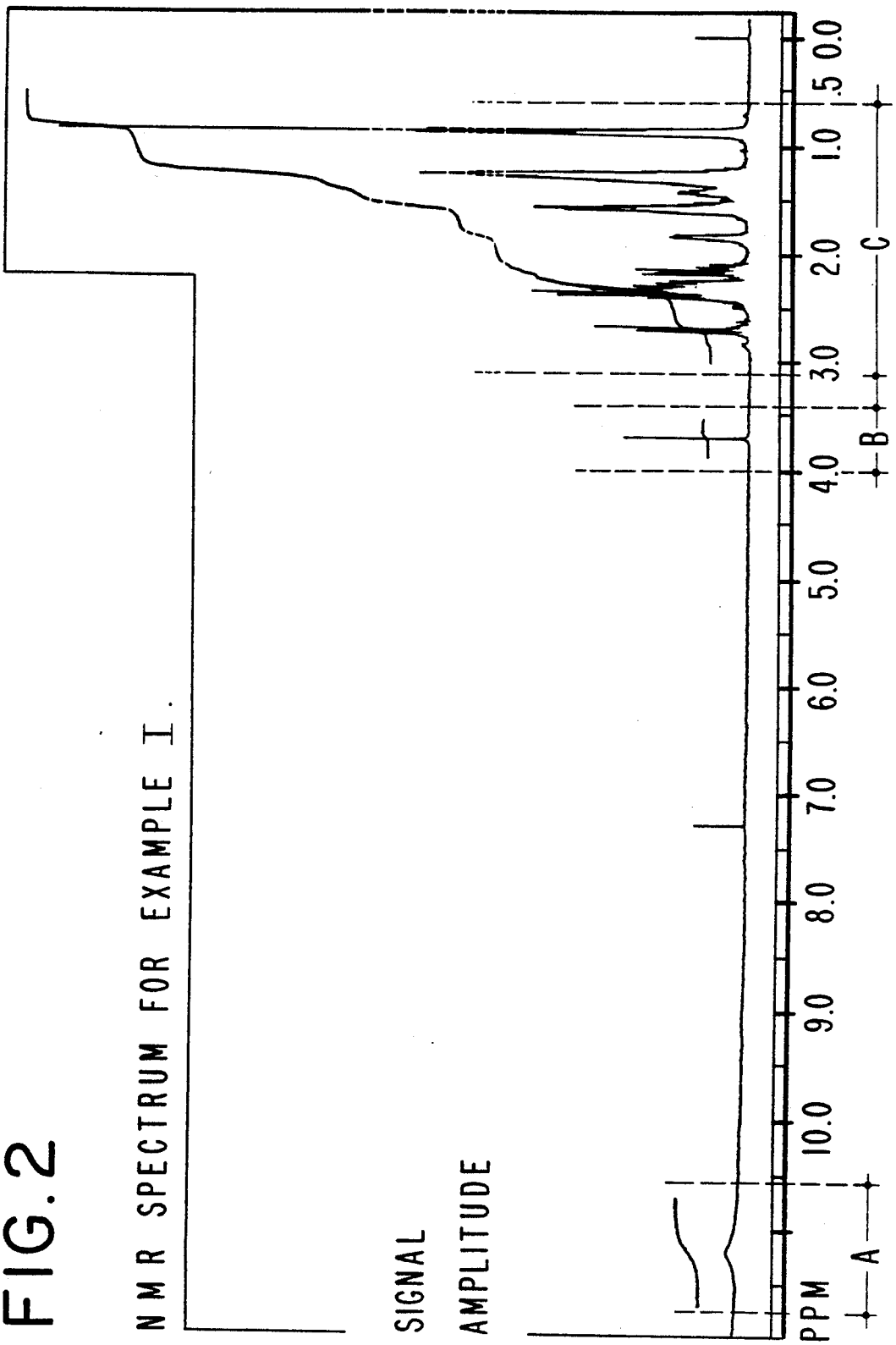

FIG.2-A
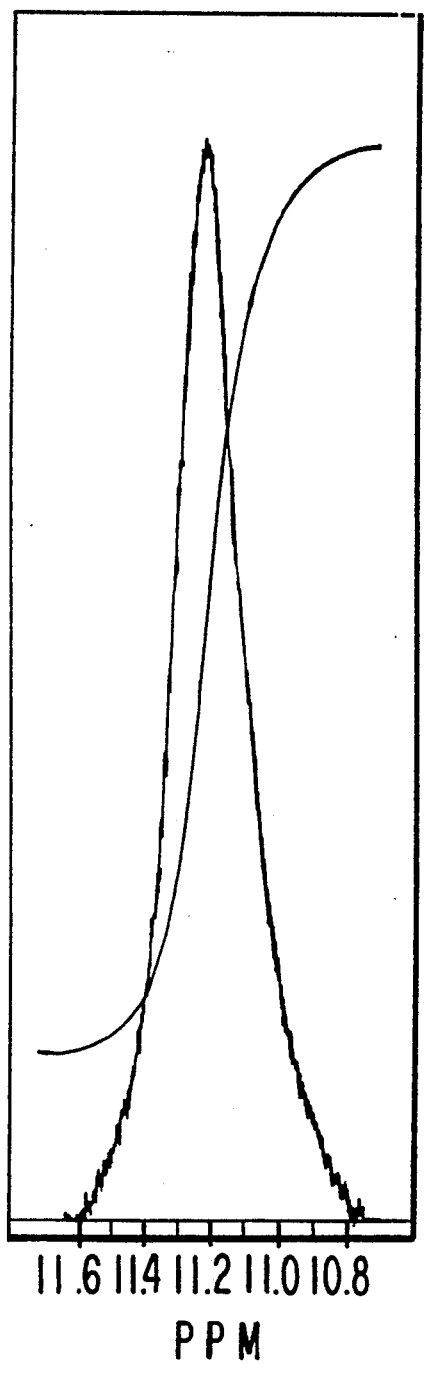
PPM
FIG.2-B
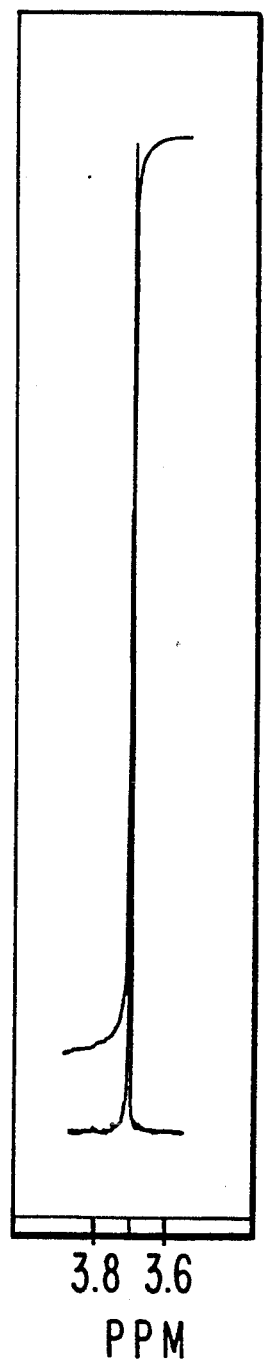
PPM

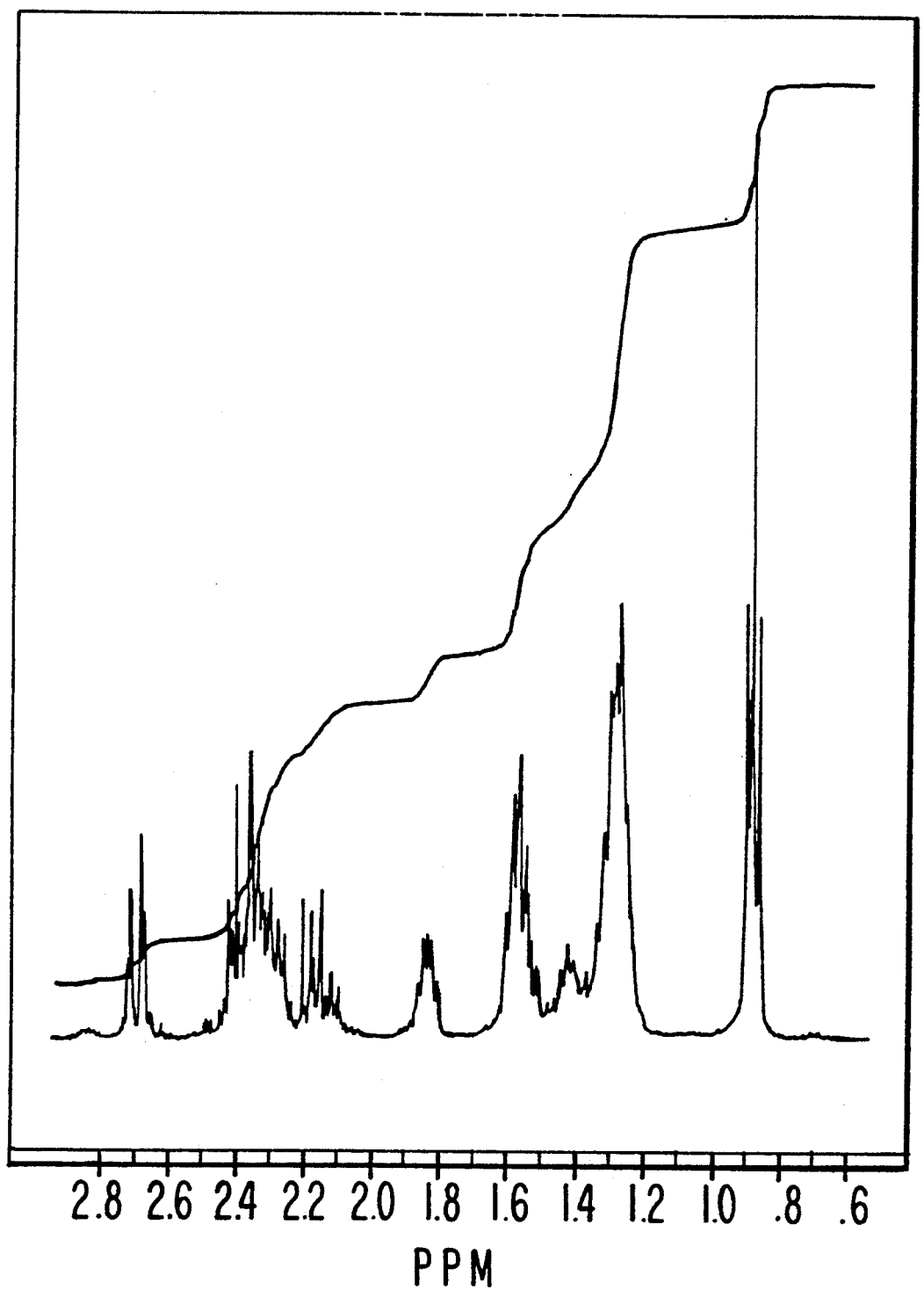
FIG.2-C

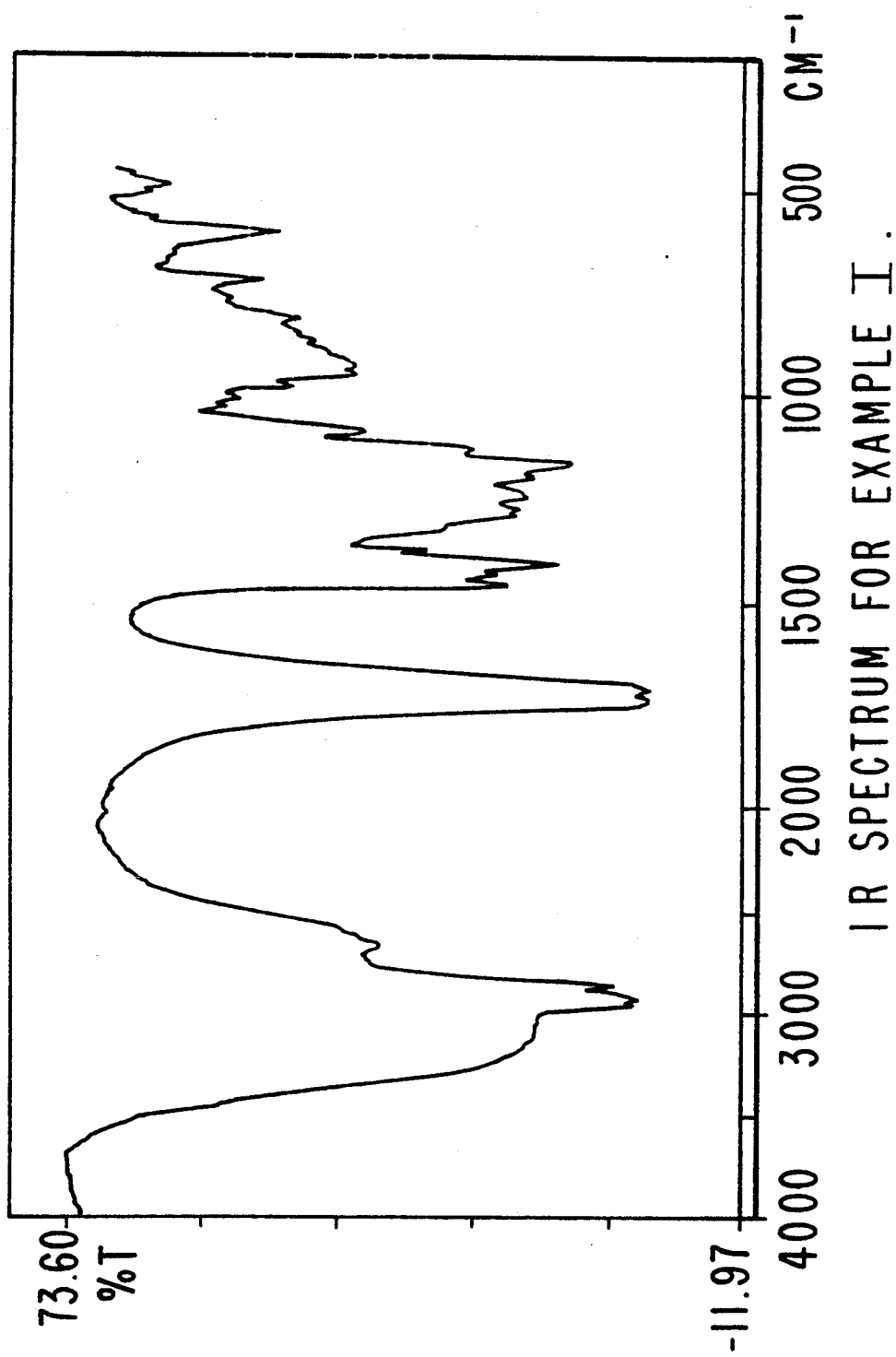

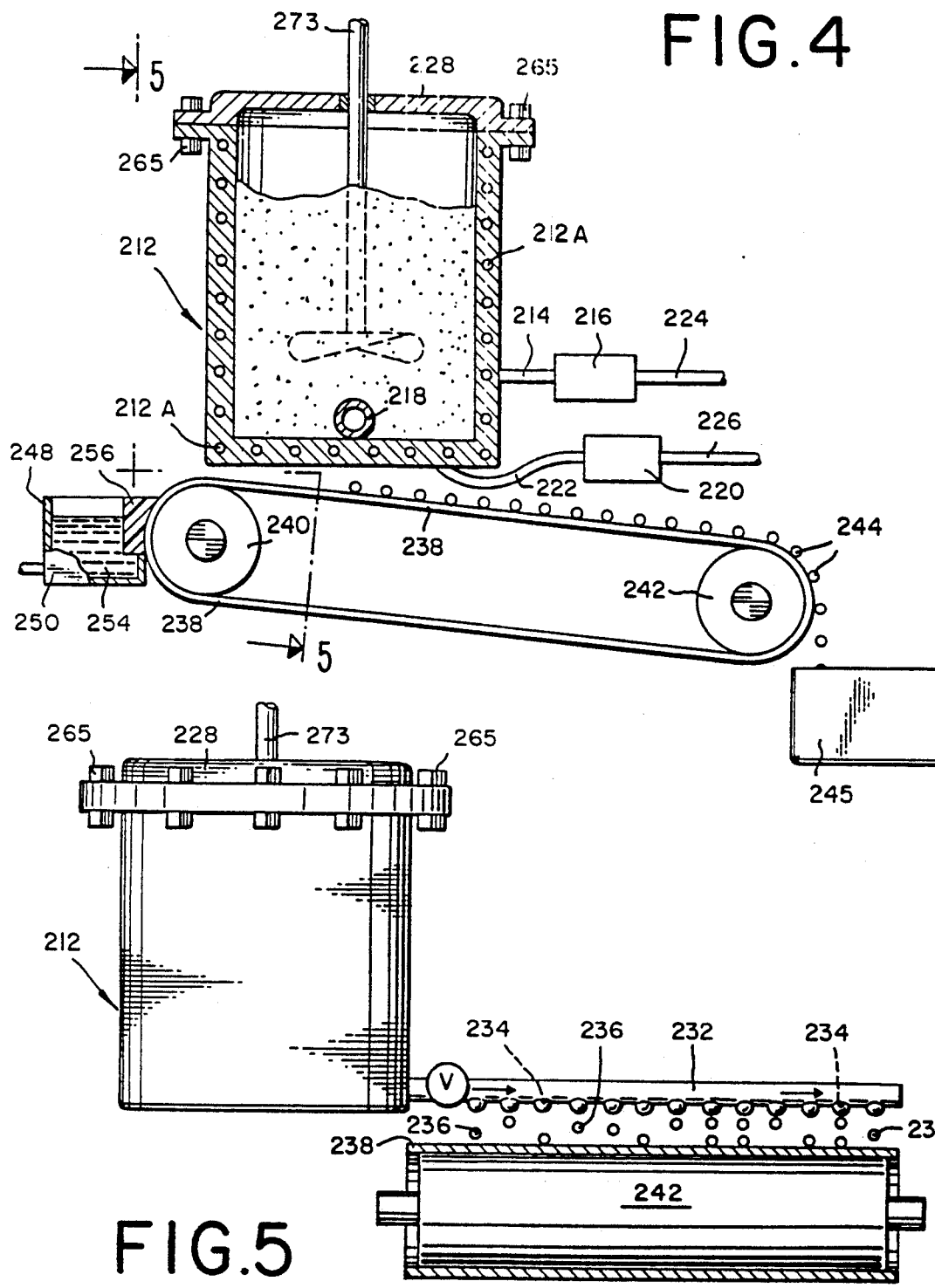

FRAGRANCE USE OF DIHYDROMETHYL JASMONIC ACID

BACKGROUND OF THE INVENTION

Dihydromethyl jasmonic acid having the structure:

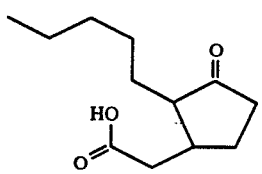

is known as an intermediate in the preparation of dihydromethyl jasmonate having the structure:

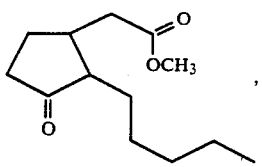

a known perfumery material. However, the perfume use of the intermediate, dihydromethyl jasmonic acid is unknown and, in fact, its perfumery properties are unexpected, unobvious and advantageous over the ester having known use in perfumery.

The dihydromethyl jasmonic acid having the structure:

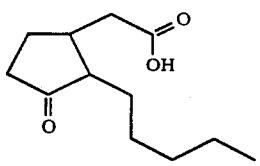

is shown to be useful as an intermediate in a paper by Ravid and Ikan, J. Org. Chem., Volume 39, No. 17, 1974, pages 2637–2639.

BRIEF DESCRIPTION OF THE DRAWINGS

FIG. 1 is the GLC profile of the reaction product of Example I containing the compound having the structure:

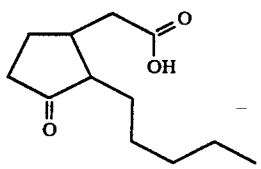

FIG. 2 is the NMR spectrum for the compound having the structure:

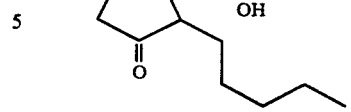

prepared according to Example I.

FIGS. 2A, 2B and 2C are enlargements of sections "A", "B" and "C" of the NMR spectrum of FIG. 2.

FIG. 3 is the infra-red spectrum for the compound having the structure:

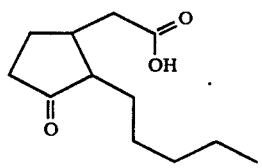

prepared according to Example I.

FIG. 4 represents a cut-away side elevation view of apparatus used in forming perfumed polymers which contain imbedded in the intersities thereof the dihydromethyl jasmonic acid of our invention.

FIG. 5 is a front view of the apparatus of FIG. 4 looking in the direction of the arrows.

DETAILED DESCRIPTION OF THE DRAWINGS

FIG. 1 is the GLC profile for the distillation Fraction 4 of the reaction product of Example I. The peak indicated by reference numeral 12 is the peak for the compound having the structure:

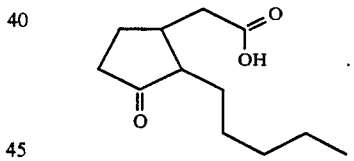

The peak indicated by reference numeral 10 is the peak for the precursor having the structure:

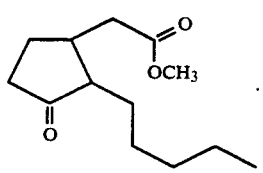

Referring to FIGS. 4 and 5 there is provided a process for forming scented polymer pellets (wherein the polymer may be a thermoplastic polymer such as low density polyethylene or polypropylene or copolymers of ethylene and vinyl acetate or mixtures of polymers and copolymers such as copolymers of ethylene and vinyl acetate and, in addition, polyethylene) such as pellets useful in the formation of plastic particles, useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 4 and 5, in particular, the apparatus used in producing such elements comprises a device for forming the polymer containing perfume, e.g., polyethylene or polyethylene/polyvinyl acetate or mixtures of same or polypropylene, which comprises a vat or container 212 into which the polymer taken alone or in admixture with other copolymers and the perfuming substance which is at least the dihydromethyl jasmonic acid of our invention and other compatible perfumes, is placed. The container is closed by means of an air-tight lid 228 and clamped to the container by bolts 265. A stirrer 273 traverses the lid or cover 228 in an air-tight manner and is rotatable in a suitable manner. A surrounding cylinder having heating coils 212A which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90-100 sayboldt seconds. The heater 218 is operated to maintain the upper portion of the container 212 within a temperature range of, for example, 220°-270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition or perfume material which contains at least the dihydromethyl jasmonic acid of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes, and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with at least the dihydromethyl jasmonic acid of our invention will continuously drop through the orifices of 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is at least the dihydromethyl jasmonic acid of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides the compound dihydromethyl jasmonic acid having the structure:

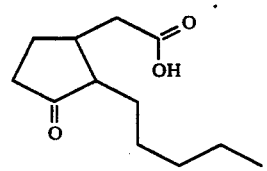

and uses thereof in augmenting, enhancing or imparting an aroma in or to perfume compositions, colognes and perfumed articles, (e.g., solid or liquid anionic, cationic, nonionic or zwitterionic detergents, fabric softener compositions, fabric softener articles, perfumed polymers and cosmetic powders).

Also described is a process for preparing the dihydromethyl jasmonic acid having the structure:

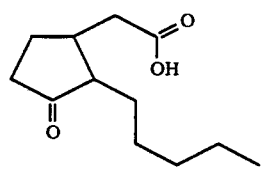

using as a starting material dihydromethyl jasmonate esters having the generic structure:

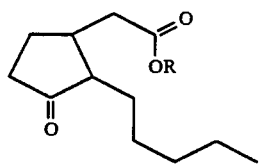

wherein R represents lower alkyl such as methyl.

The dihydromethyl jasmonic acid may, for example, be prepared from HEDIONE ® having the structure:

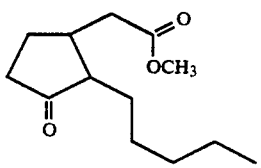

or it may be prepared from other alkyl esters of dihydromethyl jasmonic acid having the generic structure:

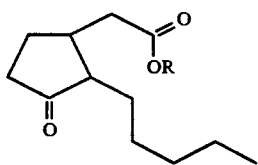

wherein R represents lower alkyl according to the reactions:

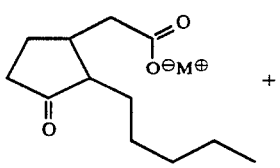

+ MOH ⟶

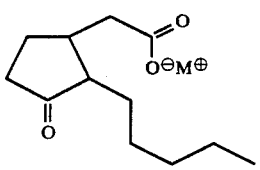

and

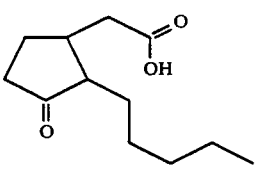

+ H₃O⊕ ⟶

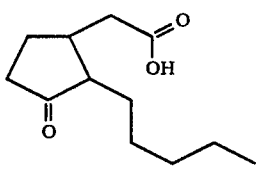

wherein M represents alkali metal such as sodium, potassium or lithium. In the alternative the compound having the structure:

may be prepared using 2-pentyl-3-dimethyl malonyl cyclo-pentan-1-one according to the process set forth by Ravid and Ikan, J.Org.Chem., Volume 39, No. 17, 1974, pages 2637–2639, the details of the process being set forth at the column bridging pages 2738 and 2739. The disclosure of the Ravid and Ikan article is incorporated herein by reference.

With reference to the reaction:

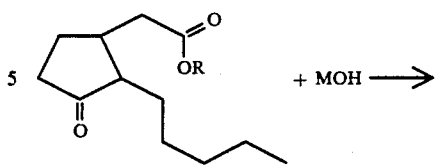

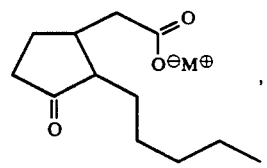

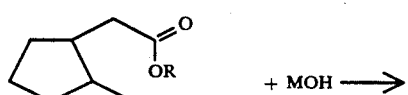

this reaction is carried out in the presence of a volatile alcohol such as methyl alcohol at reflux conditions (in the case of methyl alcohol:67°–72° C. at atmospheric pressure) for a period of time of from about two hours up to about six hours at atmospheric pressure. At the end of the reaction the reaction mass is extracted with an organic solvent such as toluene and the toluene extract is acidified with, for example aqueous hydrochloric acid. The resultant product is then reextracted with another organic solvent such as toluene and the resulting product is evaporated (removing the solvent) and the evaporated substance is then fractionally distilled yielding the dihydromethyl jasmonic acid having the structure:

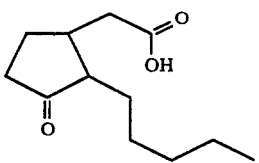

which distills at about 190° C. vapor temperature at 1 mm/Hg. pressure. The resulting distillate has in it a major proportion of the compound having the structure:

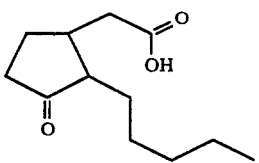

and a minor proportion of ester, for example, the compound having the structure:

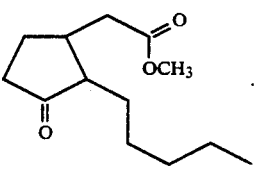

This mixture may be used "as is" for perfumery purposes or it may be further fractionally distilled to yield pure compound having the structure:

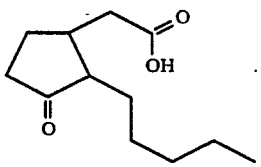

Our invention is intended to cover from about 90% up to about 100% dihydromethyl jasmonic acid having the structure:

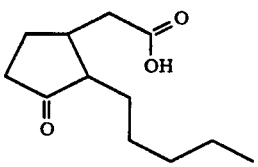

and from 0 up to 10% of esters having the structure:

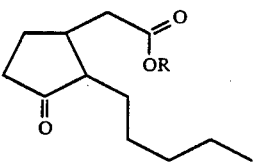

wherein R is $C_1$–$C_4$ lower alkyl. Most preferably, our invention is intended to cover mixtures of compounds and the pure compound having the structure:

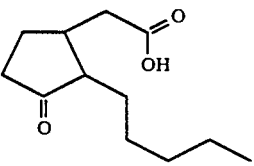

wherein the mixtures contain from 0 up to 10% by weight of the compound having the structure:

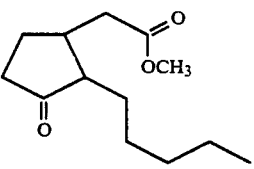

and from 90 up to 100% by weight of the compound having the structure:

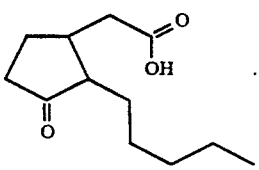

Thus, the mixtures contain from 0.1 up to 10.0% of the compound having the structure:

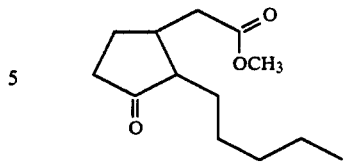

and from 90% up to 99.9% of the compound having the structure:

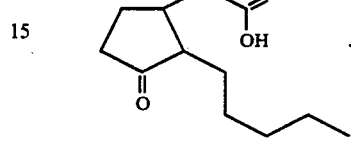

The mixtures set forth above and the compound having the structure:

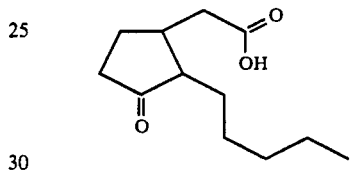

have unexpected, unobvious and advantageous perfumery properties; particularly in the jasmine perfume and jasmine/galbanum perfume area.

The dihydromethyl jasmonic acid prepared in accordance with the process of our invention, and the mixtures of dihydromethyl jasmonic acid with dihydromethyl jasmononate of our invention having the structure:

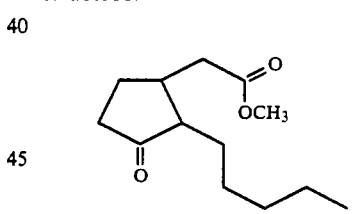

and one or more auxiliary perfume ingredients including, for example, alcohols, aldehydes, terpenic hydrocarbons, ketones other than the compositions of our invention, esters, lactones, natural essential oils, synthetic essential oils, mercaptans and alkyl mercapto derivatives may be admixed so that the combined odors of the individual components produce a pleasant and desired fragrance, particularly and preferably in the floral type fragrances (specifically, for example, the jasmine/galbanum fragrances). Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual compositions which contribute to their particular olfactory, characteristics. However, the over-all sensory effect of the perfume composition will be at least the sum total of the effects of each of the ingredients. Thus, the dihydromethyl jasmonic acid of our invention or mixtures of the dihydromethyl jasmonic acid taken together with the compound having the structure:

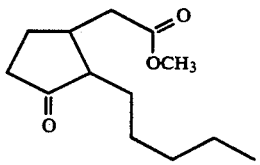

of our invention can be used to alter, modify, or enhance the aroma characteristics of a perfume composition, for example, by utilizing or moderating the olfactory reaction contributed by another ingredient in the composition.

The amount of the dihydromethyl jasmonic acid of our invention or the mixtures of dihydromethyl jasmonic acid with the compound having the structure:

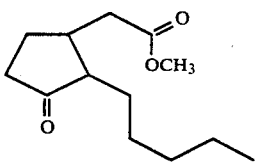

of our invention which will be effective in perfume compositions as well as in perfumed articles (e.g., solid or liquid soaps, fabric softener compositions, drier-added fabric softener articles, optical brightener compositions, perfume polymers and textile sizing agents and colognes) depends on many factors, including the other ingredients, their amounts and the effects which are desired. It has been found that perfume compositions containing as little as 0.01% of the dihydromethyl jasmonic acid of our invention or as little as 0.02% of mixtures of the dihydromethyl jasmonic acid taken together with the compound having the structure:

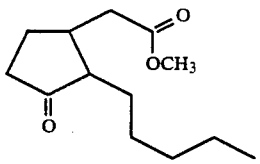

of our invention, or even less (e.g., 0.005%) can be used to impart an intense floral, muguet, jasmine, fatty and green aroma profile with fresh, floral, muguet, jasmine, green, fatty, citrusy and lemon topnotes to soaps, cosmetics, anionic, cationic, nonionic or zwitterionic detergents, fabric softener compositions, fabric softener articles, optical brightener compositions, textile sizing compositions, perfumed polymers or other products The amount employed can range up to 70% or even 100% of the fragrance components and will depend on considerations of cost, nature of the end product, the effect desired on the finished product and the particular fragrance sought.

The dihydromethyl jasmonic acid of our invention or the mixtures of dihydromethyl jasmonic acid with the compound having the structure:

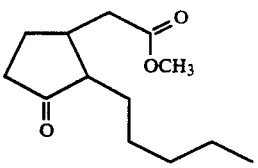

of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers When used as (an) olfactory component of a perfumed article, as little as 0.2% of the dihydromethyl jasmonic acid of our invention or mixtures of the dihydromethyl jasmonic acid with the compound having the structure:

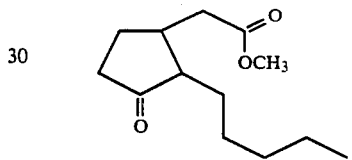

of our invention will suffice to impart highly intense floral, muguet, jasmine, fatty and green aromas, with fresh, floral, muguet, jasmine, green, fatty, citrusy and lemony topnotes to floral perfume formulations. Generally, no more than 6% of the dihydromethyl jasmonic acid of our invention or mixtures of dihydromethyl jasmonic acid with the compound having the structure:

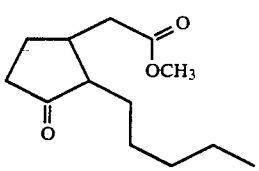

of our invention based on the ultimate end product is required in the perfumed article composition. Accordingly, the range of the dihydromethyl jasmonic acid of our invention or mixtures of dihydromethyl jasmonic acid with the compound having the structure:

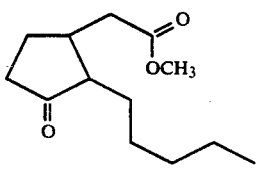

of our invention in the perfumed article is from about 0.2% by weight of the dihydromethyl jasmonic acid or mixtures of dihydromethyl jasmonic acid with the compound having the structure:

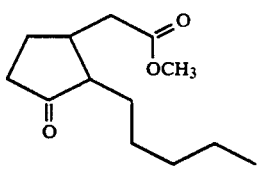

up to about 6% by weight based on the perfumed article. In addition, the perfume composition or fragrance composition of our invention can contain a vehicle or carrier for the dihydromethyl jasmonic acid of our invention or the mixture of dihydromethyl jasmonic acid with the compound having the structure:

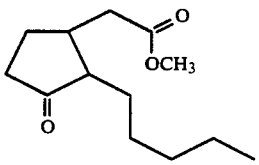

of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic, guar gum or xantham gum) or components for encapsulating the composition (such as gelatin) as by coacervation; or components for forming a polymer wall around a liquid perfume center such as a urea formaldehyde prepolymer.

Our invention also relates to the utilization of controlled release technology for the controlled release of perfumes into gaseous environments from polymers such as mixtures of epsilon polycaprolactone polymers and polyethylene which poly epsilon caprolactone polymers are defined according to the structure:

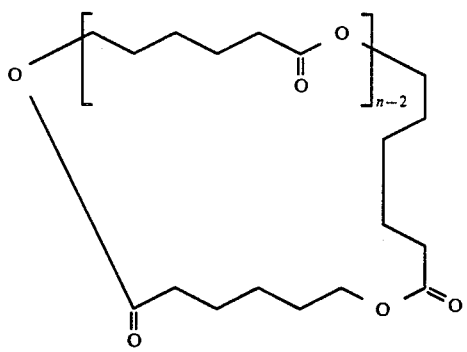

wherein "n" is from about 50 up to about 1,200 with the proviso that the average "n" in the system varies from about 150 up to about 700 according to the mathematical statement:

$$700 \geq n \geq 150$$

with the term n being the average number of repeating monomeric units for the epsilon polycaprolactone polymer The perfumed material's release rate from such polymer mixture is close to "zero order". As a general rule, the release rate in a polymeric matrix is proportional to t-½until about 60% of the functional fluid is released from the polymeric matrix. The release rate thereafter is related exponentially to time as a general rule according to the equation:

$$\frac{dM_1}{dt} = k_1 e^{-k_2 t}$$

wherein $K_1$ and $k_2$ are constants. According to Kydonieus, "Controlled Release Technologies Methods, Theory, and Applications" (cited, supra), the amount of perfume composition released is proportional to time as long as the concentrations of perfume material present, e.g., the dihydromethyl jasmonic acid of our invention or the mixture of dihydromethyl jasmonic acid with the compound having the structure:

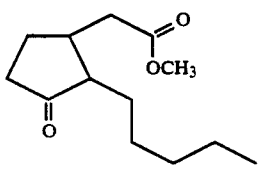

of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the dihydromethyl jasmonic acid of our invention or the mixtures of dihydromethyl jasmonic acid with the compound having the structure:

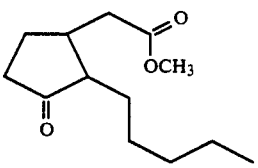

of our invention or the mixtures of dihydromethyl jasmonic acid with the compounds having the structure:

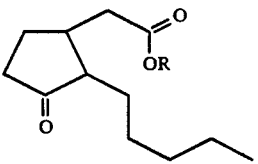

of our invention wherein R represents $C_1$-$C_4$ lower alkyl.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such as hydroquinone or compounds having the formula:

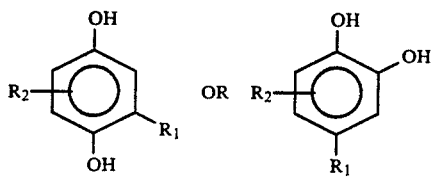

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or adsorbed into the polymeric matrix.

The method for incorporating the dihydromethyl jasmonic acid of our invention or the mixtures of dihydromethyl jasmonic acid with the compound having the structure:

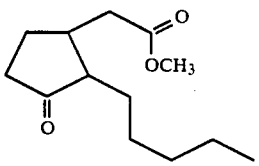

of our invention or the mixtures of dihydromethyl jasmonic acid with the compounds having the structure:

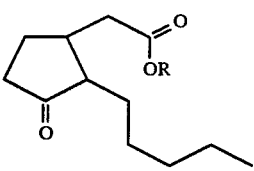

of our invention wherein R represents $C_1$-$C_4$ lower alkyl, or perfume compositions containing same into polymers may be produced according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene-polyepsilon caprolactone polymer mixture (50:50) is mixed with the dihydromethyl jasmonic acid of our invention or the mixtures of dihydromethyl jasmonic acid with the compound having the structure:

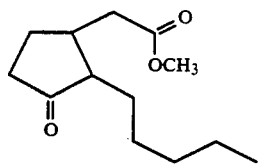

of our invention or the mixtures of dihydromethyl jasmonic acid with the compounds having the structure:

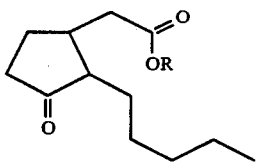

of our invention wherein R represents $C_1$-$C_4$ lower alkyl. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of a scent is effected in two stages. In a first stage, a 50:50 (weight:weight) polyepsilon caprolactone, e.g., PCL-700: polyethylene in molten form is admixed with high percentage of the dihydromethyl jasmonic acid of our invention or the mixtures of dihydromethyl jasmonic acid with the compound having the structure:

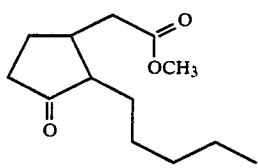

of our invention or the mixtures of dihydromethyl jasmonic acid with the compounds having the structure:

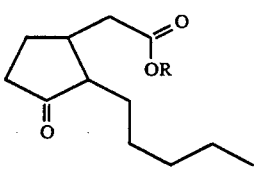

of our invention wherein R represents $C_1$-$C_4$ lower alkyl and the mixture is solidified in the form of pellets or beads. These pellets or beads thus contain a high percentage of dihydromethyl jasmonic acid of our invention or the mixtures of dihydromethyl jasmonic acid with the compound having the structure:

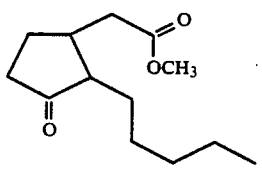

of our invention or the mixtures of dihydromethyl jasmonic acid with the compounds having the structure:

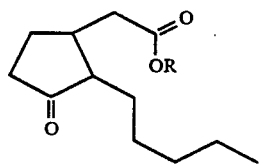

of our invention wherein R represents $C_1$–$C_4$ lower alkyl (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention the dihydromethyl jasmonic acid of our invention or the mixtures of dihydromethyl jasmonic acid with the compound having the structure:

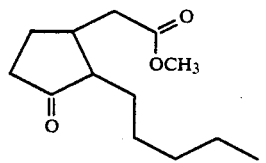

of our invention or the mixtures of dihydromethyl jasmonic acid with the compounds having the structure

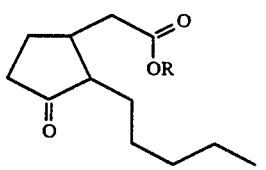

of our invention wherein R represents $C_1$–$C_4$ lower alkyl is added to the polymer in a large closed container or drum which is maintained under controlled temperature conditions while the polymer in a melted condition is mixed with the dihydromethyl jasmonic acid of our invention or the mixtures of dihydromethyl jasmonic acid with the compound having the structure:

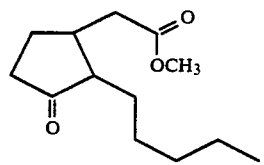

of our invention or the mixtures of dihydromethyl jasmonic acid with the compounds having the structure:

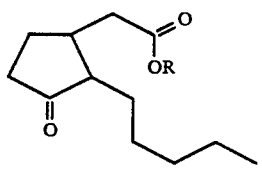

of our invention wherein R represents $C_1$–$C_4$ lower alkyl under agitation.

The following Example I serves to illustrate a process for preparing the compound having the structure:

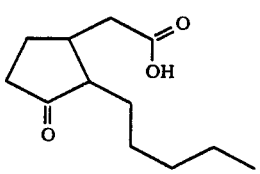

of our invention.

The examples following Example I are illustrative of the organoleptic utilities of the compound having the structure:

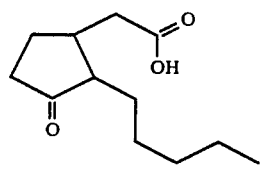

or mixtures of compounds having the structure:

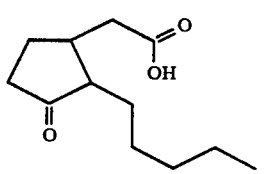

and the compounds having the structure:

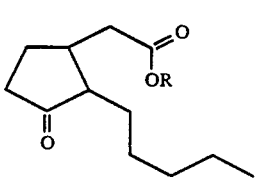

wherein R represents $C_1$–$C_4$ lower alkyl of our invention.

EXAMPLE I

Preparation of Dihydromethyl Jasmonic Acid

Reactions:

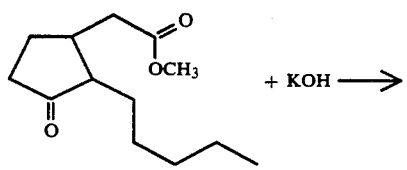   + KOH ⟶

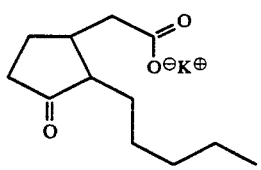

and

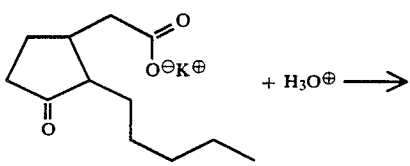   + H₃O⊕ ⟶

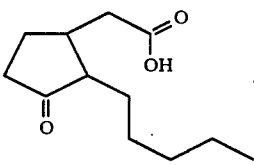

Into a 3 liter reaction vessel equipped with stirrer, thermometer and reflux condenser are placed 198 grams of potassium hydroxide; 500 grams water; 1,000 grams of methyl alcohol; and 452 grams of the compound having the structure:

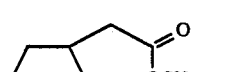

The reaction mass is heated to reflux under a nitrogen blanket and refluxing is continued for a period of four hours at 69°–72° C. At the end of the four hour period, the reaction mass is continued to be stirred for an additional twelve hours while maintaining the temperature at 70° C.

750 ml Anhydrous toluene is then added to the reaction mass which is stirred for 15 minutes. The reaction mass is then transferred to a separatory funnel and the organic layer is separated from the aqueous phase. The organic layer is removed and the aqueous layer is placed back into the reaction vessel and admixed with 305 ml of concentrated aqueous hydrochloric acid. The resulting reaction mass is stirred for a period of one hour. The reaction mass is then extracted with 500 ml toluene. The extracted product weighing 909.3 grams is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 47 | 66 | 316 |
| 2 | 52 | 105 | 185 |
| 3 | 40 | 130 | 4 |
| 4 | 190 | 200 | 1 |
| 5 | 120 | 220 | 2. |

FIG. 1 is the GLC profile for Fraction 4. Fraction 4 has an intense floral, muguet, jasmine, fatty and green aroma with fresh, floral, muguet, jasmine, green, fatty, citrusy and lemony topnotes. Fraction 4 contains 10% of the compound having the structure:

and 90% of the compound having the structure:

On further careful fractional distillation of Fraction 4 at 1.0 mm/Hg. and 192° C., 99.9% of the compound having the structure:

is produced. This material has an intense muguet, jasmine aroma profile with intense and highly substantive muguet, jasmine topnotes.

EXAMPLE II
CHAMOMILE FORMULATION

The following chamomile formulations are prepared:

| Ingredients | Example II(A) | Example II(B) |
|---|---|---|
| Compound having the structure: | 24.0 | 0.0 |

(99.9% by

-continued

EXAMPLE II
CHAMOMILE FORMULATION

The following chamomile formulations are prepared:

| Ingredients | Example II(A) | Example II(B) |
|---|---|---|
| weight) prepared according to Example I. Mixture of compound having the structure: | 0.0 | 24.0 |

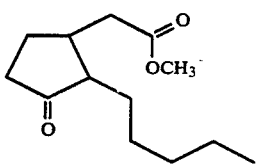

(10%)
and compound having the structure:

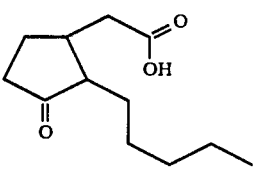

| | | |
|---|---|---|
| (90%), distillation Fraction 4 of Example I, supra. | | |
| Geraniol | 4.0 | 4.0 |
| Citronellol | 4.0 | 4.0 |
| Oil of Chamomile | 12.0 | 12.0 |

The product of Example II(A) has an excellent chamomile aroma with intense, substantive muguet and jasmine topnotes and intense and substantive muguet and jasmine undertones. Accordingly, the perfume composition of Example II(A) can be described as "a chamomile aroma with muguet and jasmine topnotes and muguet and jasmine undertones".

The product of Example II(B) has "a chamomile aroma with strong, floral, muguet, jasmine, fatty and green undertones and strong, fresh, floral, muguet, jasmine, fatty, green, citrusy and lemony topnotes".

EXAMPLE III

Preparation of Cosmetic Powder Composition

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| The compound at a level of 99.99% having the structure:<br />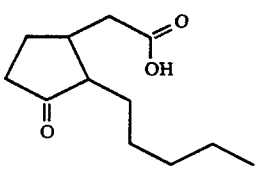 | An intense and substantive muguet and jasmine aroma with muguet and jasmine topnotes. |
| prepared according to Example I. Mixture of compounds having the structure:<br />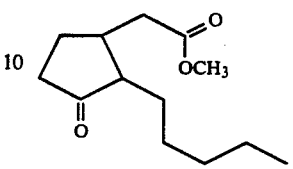<br />(10%)<br />and<br />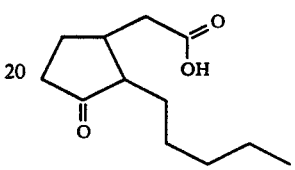<br />(90%)<br />prepared according to distillation Fraction 4 of Example I, supra. | A strong, floral, muguet, jasmine, fatty and green aroma with fresh, floral, muguet, jasmine, green, fatty, citrusy and lemony topnotes. |
| Perfume composition of Example II (A). | A chamomile aroma with muguet and jasmine topnotes and muguet and jasmine undertones. |
| Perfume composition of Example II (B). | A chamomile aroma with strong, floral, muguet, jasmine, fatty and green undertones and strong, fresh, floral, muguet, jasmine, fatty, green, citrusy and lemony topnotes. |

EXAMPLE IV

Perfumed Liquid Detergents

Concentrated liquid detergents (lysine salt of n-dodecyl-benzene sulfonic acid as more specifically described in U.S. Pat. No. 3,948,818 issued on Apr. 6, 1976 incorporated by reference herein) with aroma nuances as set forth in Table I of Example III, supra, are prepared containing 0.10%, 0.15%, 0.20%, 0.25%, 0.30% and 0.35% of the substance as set forth in Table I of Example III, supra. They are prepared by adding and homogeneously mixing the appropriate quantity of substance set forth in Table I of Example III, supra, in the liquid detergent. The detergents all possess excellent aromas as set forth in Table I of Example III, supra, the intensity increasing with greater concentrations of substance as set forth in Table I of Example III, supra.

EXAMPLE V

Preparation of Colognes and Handkerchief Perfumes

Compositions as set forth in Table I of Example III, supra, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III, supra, are imparted to the colognes and to the handkerchief perfumes at all levels indicated.

EXAMPLE VI

Preparation of Soap Compositions

One hundred grams of soap chips (per sample)-(IVORY ®, produced by the Procter & Gamble Company of Cincinnati, Ohio), are each mixed with one gram samples of substances as set forth in Table I of Example III, supra, until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III, supra.

EXAMPLE VII

Preparation of Solid Detergent Compositions

Detergents are prepared using the following ingredients according to Example I of Canadian Patent No. 1,007,948 (incorporated herein by reference):

| Ingredient | Percent by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, brighteners | q.s. |

The detergent is a phosphate-free detergent. Samples of 100 grams each of this detergent are admixed with 0.10, 0.15, 0.20 and 0.25 grams of each of the substances as set forth in Table I of Example III, supra. Each of the detergent samples has an excellent aroma as indicated in Table I of Example III, supra.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20-22}$ HAPS;
   22%—isopropyl alcohol;
   20%—antistatic agent; and
   1%—of one of the substances as set forth in Table I of Example III, supra.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III, supra, is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| Ingredients | Weight Percent |
|---|---|
| Dioctyl substrate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table I of Example III, supra. | 0.10 |

The perfume substances as set forth in Table I of Example III, supra, add aroma characteristics as set forth in Table I of Example III, supra, which are rather intense and aesthetically pleasing to the users of the soft-feel, good-hold pump hair sprays.

EXAMPLE X

Conditioning Shampoos

Monoamid CMA (prepared by the Mona Industries Company)(3.0 weight percent) is melted with 2.0 weight percent coconut fatty acid (prepared by the Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT ®755N polymer (manufactured by GAF Corporation of 140 West 51st Street, New York, N.Y.(5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table I of Example III, supra, is added to the mixture. The resulting mixture is cooled to 40° C and blending is carried out for an additional one hour in each case. At the end of this blending period, the resulting material has a pleasant fragrance as indicated in Table I of Example III, supra.

EXAMPLE XI

Each of the fragrance materials of Table I of Example III, supra, are added to a 50:50 weight:weight mixture of low density polyethylene:polyepsilon caprolactone PCL-700 forming scented pellets with scents as set forth in Table I of Example III, supra.

Using the apparatus of U.S. Pat. No. 3,505,432 issued on Apr. 7, 1970 (the specification of which is incorporated herein by reference), 75 pounds of a 50:50 mixture of PCL-700 polyepsilon caprolactone (manufactured by the Union Carbide Corporation of New York, N.Y.) having a melting point of about 180°-190° F.: Low density polyethylene, are heated to about 250° F. 25 Pounds of each of the fragrance materials as set forth in Table I of Example III, supra, is then quickly added to the liquified polymer mixture. The temperature is then raised to about 250° F. and the mixing is effected for 5-15 minutes. The molten polymer enriched with perfume ingredient is then formed into polymer beads or pellets having pronounced scents as described in Table I of Example III. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table I of Example III, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table I of Example III, supra.

What is claimed is:

1. A perfume composition comprising a perfume base and intimately admixed therewith an aroma imparting, augmenting or enhancing quantity of a mixture of compounds having the structures:

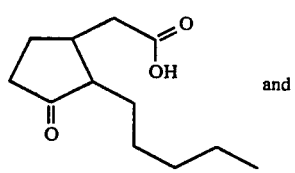

and

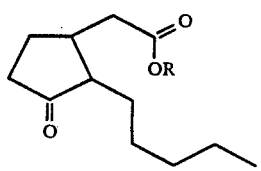

wherein R represents $C_1$-$C_4$ lower alkyl; wherein the compound having the structure:

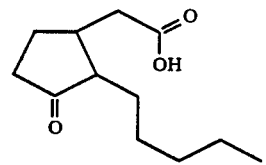

is present in an amount of from 90% up to 99.9% and the compounds having the structure:

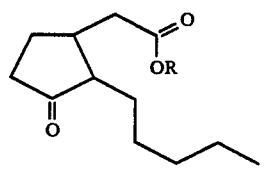

are present in an amount of from 0.1% up to 10% by weight of the mixture.

2. The perfume composition of claim 1 wherein R is methyl.

3. A perfumed article comprising a perfumed article base and intimately admixed therewith an aroma augmenting, enhancing or imparting quantity of a mixture of compounds having the structures:

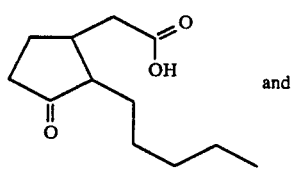 and

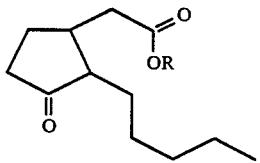

wherein R represents $C_1$-$C_4$ lower alkyl; wherein the compound having the structure:

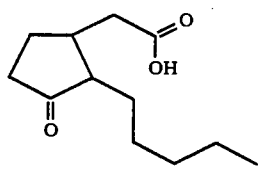

is present in an amount of from 90% up to 99.9% and the compounds having the structure:

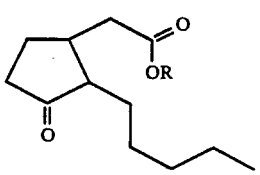

are present in an amount of from 0.1% up to 10% by weight of the mixture.

4. The perfumed article of claim 3 wherein R is methyl.

5. A perfumed polymer comprising a microporous polymer and contained in the interstices thereof an aroma augmenting, enhancing or imparting quantity of a mixture of compounds having the structures:

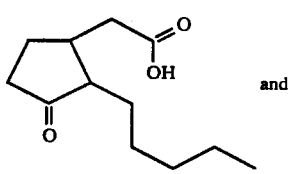
and

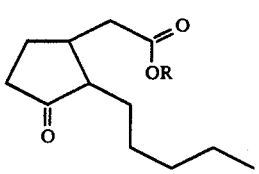

wherein R represents $C_1$-$C_4$ lower alkyl; wherein the compound having the structure:

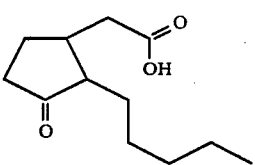

is present in an amount of from 90% up to 99.9% and the compounds having the structure:

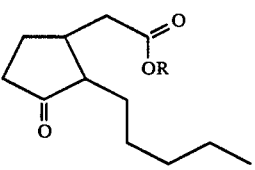

are present in an amount of from 0.1% up to 10% by weight of the mixture.

6. The perfumed article of claim 5 wherein R is methyl.

7. A process for augmenting, enhancing or imparting an aroma in or to a perfume composition, cologne or perfumed article comprising the step of intimately admixing with said perfume composition, cologne or perfumed article an aroma augmenting, imparting or enhancing quantity of a mixture of compounds having the structures:

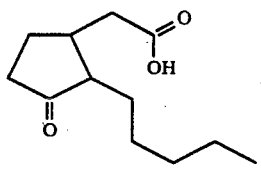
and

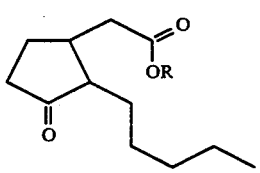

wherein R represents $C_1$-$C_4$ lower alkyl; wherein the compound having the structure:

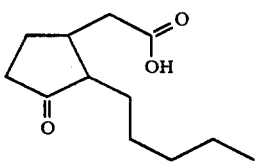

is present in an amount of from 90% up to 99.9% and the compounds having the structure:

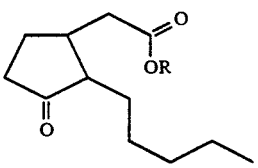

are present in an amount of from 0.1% up to 10% by weight of the mixture.

8. The process of claim 7 wherein R is methyl.

9. A cologne consisting essentially of ethanol, water and a perfume composition defined according to claim 1.

10. The cologne of claim 9 wherein R is methyl.

* * * * *